United States Patent [19]

Treuner et al.

[11] 4,113,943
[45] Sep. 12, 1978

[54] 7β-[(2-AMINO-1,2-DIOXOETHYL)AMINO]A-CYL CEPHALOSPORINS

[75] Inventors: Uwe D. Treuner; Hermann Breuer, both of Regensburg, Germany

[73] Assignee: E. R. Squibb & Sons, Inc., Princeton, N.J.

[21] Appl. No.: 776,400

[22] Filed: Mar. 10, 1977

[51] Int. Cl.$^2$ .......................................... C07D 501/36
[52] U.S. Cl. ...................... 544/26; 562/450; 562/507; 562/561; 544/19; 544/21; 544/27; 544/30; 544/4; 424/246; 560/41; 560/125; 560/171; 560/142; 260/332.2 R; 260/347.4; 560/169
[58] Field of Search ....................... 544/19, 21, 26, 27, 544/30, 4

[56] References Cited

U.S. PATENT DOCUMENTS 3,573,294  3/1971  Long et al. ...................... 424/246
4,028,354  6/1977  Breuer et al. ................... 260/243 C Primary Examiner—Donald G. Daus
Assistant Examiner—David E. Wheeler
Attorney, Agent, or Firm—Lawrence S. Levinson; Merle J. Smith

[57] ABSTRACT

7β-[(2-Amino-1,2-dioxoethyl)amino]acyl cephalosporins of the formula

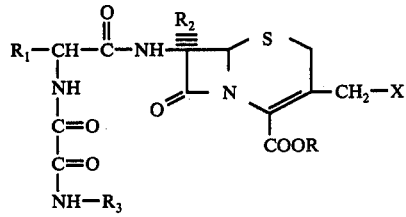

wherein R is hydrogen, lower alkyl, phenyl-lower alkyl, diphenyl-lower alkyl, tri(lower alkyl)silyl, trihaloethyl or a salt forming ion; $R_1$ is hydrogen, lower alkyl, saturated or unsaturated cycloalkyl, phenyl, phenyl-lower alkyl, substituted phenyl or certain heterocyclic groups; $R_2$ is hydrogen or methoxy; $R_3$ is hydrogen, lower alkyl or cycloalkyl; and X is hydrogen, lower alkanoyloxy, carbamoyloxy, lower alkoxy, lower alkylthio

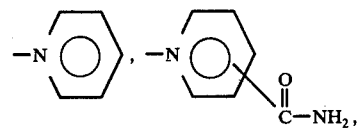

or certain heterothio groups, are useful as antibacterial agents.

12 Claims, No Drawings

7β-[(2-AMINO-1,2-DIOXOETHYL)AMINO]ACYL CEPHALOSPORINS

SUMMARY OF THE INVENTION

Cephalosporins and penicillins having a ureido and similar type acyl side chain are disclosed, for example, in U.S. Pat. Nos. 3,673,183, 3,687,949, 3,708,479, 3,833,568, 3,860,591, 3,925,368, 3,954,802, 3,956,292, 3,972,870, 3,974,140, 3,982,011 and German Offenlegungsschrift 2,513,954 and 2,514,019. Cephalosporins having various acyl side chains and a 7α-methoxy substituent are shown in various U.S. Pat. Nos. including, for example, 3,755,410, 3,780,031, 3,780,033, 3,780,034, 3,780,034, and 3,843,641, etc.

This invention relates to new 7β-[(2-amino-1,2-dioxoethyl)amino]acyl cephalosporin derivatives of the formula

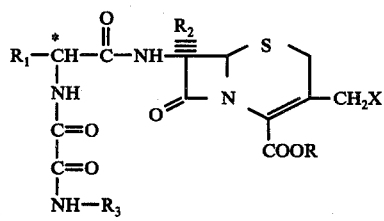

which are distinguishable from such prior known compounds.

R represents hydrogen, lower alkyl, phenyl-lower alkyl, diphenyl-lower alkyl, tri(lower alkyl)silyl, trihaloethyl or a salt forming ion.

$R_1$ represents hydrogen, lower alkyl, saturated or unsaturated cycloalkyl, phenyl, phenyl-lower alkyl, substituted phenyl or certain heterocyclic groups.

$R_2$ represents hydrogen or methoxy. The $R_2$ substituent is in the α-configuration as indicated by the broken lines.

$R_3$ represents hydrogen, lower alkyl or cycloakyl.

X represents hydrogen, lower alkanoyloxy, carbamoyloxy, lower alkoxy, lower alkylthio, certain heterothio groups,

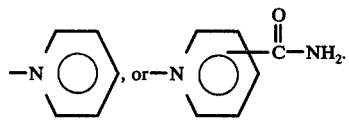

When X is pyridinium or carbamoyl substituted pyridinium, the compounds can be structurally represented as having the formula

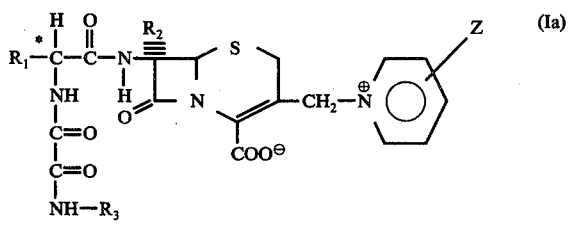 (Ia)

wherein Z is hydrogen or carbamoyl.

The asterisk indicates an asymmetric carbon atom.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 7 carbon atoms preferably 1 to 4 carbons. Examples of the type of groups contemplated are methyl, ethyl, propyl, isopropyl, butyl, t-butyl, etc. The lower alkosy and lower alkylthio groups include such lower alkyl groups attached to an oxygen of sulfur, respectively, e.g., methoxy, ethoxy, propoxy, methylthio, ethylthio, propylthio, etc. The phenyl-lower alkyl and diphenyl-lower alkyl groups include such lower alkyl groups attached to one or two phenyl rings preferably benzyl, phenethyl and diphenylmethyl.

The saturated and unsaturated cycloalkyl groups are the alicyclic groups having up to 7 carbons and up to 2 double bonds in the ring, i.e., the cycloalkyl groups cyclopropyl, cyclobutyl, cyclopentyl, cyclohexyl and cycloheptyl, the cycloalkenyl groups having up to 7 carbons with one double bond, cyclobutenyl, cyclopentenyl, cyclohexenyl and cycloheptenyl and the cycloalkadienyl groups having up to 7 carbons with two double bonds located at various positions such as 1,4-cyclohexadienyl which is preferred.

The substituted phenyl groups include one or two substituents selected from halogen (preferably chlorine or bromine), lower alkyl (preferably having 1 to 4 carbons, especially methyl or ethyl), lower alkoxy (preferably having 1 to 4 carbons especially methoxy or ethoxy), and hydroxy, e.g., 2-, 3-, or 4-chlorophenyl, 2-, 3-, or 4-bromophenyl, 2-, 3-, or 4-hydroxyphenyl, 3,5-dichlorophenyl, 2-, 3-, or 4-methylphenyl, 2-, 3- or 4-ethoxyphenyl, etc.

The salt forming ions represented by R are metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such a methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri (lower alkyl)silyl group.

The heterocyclic groups represented by $R_1$ are 2-thienyl, 3-thienyl, 2-furyl, 3-furyl, 2-pyridyl, 3-pyridyl, or 4-pyridyl.

Lower alkanoyloxy refers to a group of the formula

lower alkyl preferably wherein the lower alkyl group is methyl.

The heterothio groups represented by X are

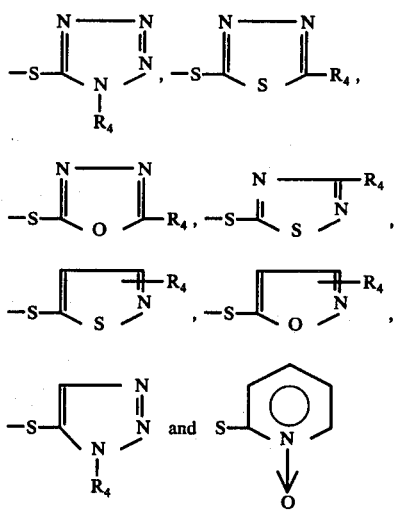

wherein R₄ is hydrogen or lower alkyl (preferably having 1 to 4 carbons especially methyl or ethyl).

The products of this invention are produced by acylating a cephem compound having the formula

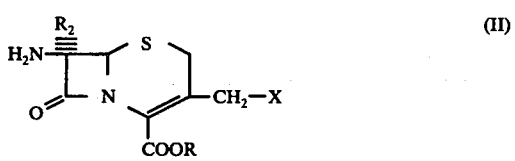

with an acid having the formula

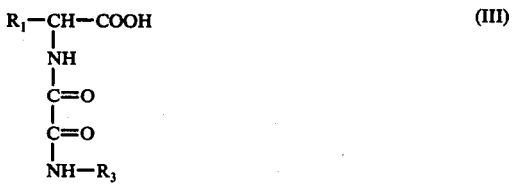

or an activated derivative like the acid halide, activated ester like the nitrophenyl ester or dinitrophenyl ester, or mixed anhydride, and/or in the presence of a coupling agent like dicyclohexylcarbodiimide.

The compound of formula II is preferably in the form of an ester, i.e., R is an easily removable group like diphenylmethyl, which is preferred, t-butyl, trimethylsilyl, etc.

One preferred synthesis comprises reacting the acid of formula III with the diphenylmethyl ester of the compound of formula II in the presence of dicyclohexylcarbodiimide and then hydrolyzing the ester with trifluoroacetic acid and anisole to obtain the free carboxyl group in the 4-position. A salt can be obtained from the acid by reaction with the base having the desired cation.

This reaction can be carried out, for example, by dissolving or suspending the acid in an inert organic solvent such as chloroform, tetrahydrofuran, methylene chloride, dioxane, benzene or the like, and adding, at a reduced temperature of about 0°–5° C., about an equimolar amount of the compound of formula II in the presence of a coupling agent such as dicyclohexylcarbodiimide. The product of the reaction is then isolated by conventional procedures, e.g., by concentration or evaporation of the solvent. If a derivative such as the diphenylmethyl ester is used, the free acid is obtained by hydrolysis, e.g., with trifluoroacetic acid and anisole or the like. Salts can then be derived from the free acid.

According to another embodiment, the acid chloride of the compound of formula III (prepared from the acid with thionyl chloride) is made to react with a compound of formula II, preferably wherein R is an easily removable group like trimethylsilyl or diphenylmethyl. When R is the diphenylmethyl group, it is converted to the free acid with trifluoroacetic acid and anisole as described above.

The compounds of formula I wherein X is pyridinium or carbamoyl substituted pyridinium can be prepared by reacting a compound of formula I wherein X is acetoxy with pyridine or carbamoyl substituted pyridine in a polar solvent such as water and in the presence of a catalyst such as an alkali metal thiocyanate by the method described in U.S. Pat. No. 3,792,047 and German Offenlegungsschrift No. 2,234,280.

Compounds of formula I wherein X is a heterothio group can also be produced by reacting a compound of formula I wherein X is acetoxy with a mercaptan of the formula

or an alkali metal (preferably sodium) salt of the formula

bu the methods described in U.S. Pat. Nos. 3,855,213; 3,890,309; and 3,892,737.

The starting material of formula III is produced from an α-amino acid ester having the formula

wherein R₁ has the same meaning as defined above and Y is a readily removable group, e.g., diphenylmethyl, nitrophenyl, dinitrophenyl, t-butyl, trimethylsilyl or the like, which is made to react with an oxalic acid derivative having the formula

wherein hal represents halogen, preferably chlorine, and Z is lower alkyl, in the presence of a base like triethylamine. This reaction yields an intermediate having the formula

Treatment of this intermediate with an acid, e.g., trifluoroacetic acid and anisole, yields the free acid having the formula

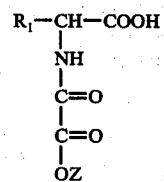

Treatment of the product of formula IX with ammonia or an amine NHR₃ and then acidifying yields the acylating agent III. Activated derivatives thereof are produced by reaction with thionyl chloride, esterifying agent, anhydride, or the like, by conventional procedures.

Alternatively, an α-amino acid ester of formula VI, preferably the diphenylmethyl ester, nitrophenyl ester or dinitrophenyl ester, is made to react with an oxalyl halide like oxalyl chloride to obtain a compound of the formula

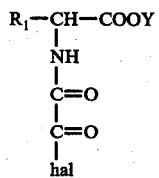

wherein hal represents halogen, preferably chlorine, and Y is one of the foregoing ester groups like diphenyl methyl, p-nitrophenyl or 2,4-dinitrophenyl. Reaction of this derivative with ammonia or an amine HN-R₃ yields a product of the formula

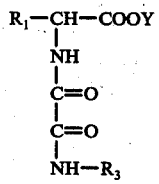

When Y is nitrophenyl or dinitrophenyl, the intermediate of formula XI can be made to react with the compound of formula II.

When Y is diphenylmethyl in formula XI it is preferable to react this intermediate with an acid, e.g., hydrochloric acid in glacial acetic acid, to form a compound of the formula

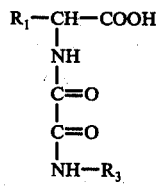

which is then made to react with the compound of formula II, preferably in the form of its diphenylmethyl ester, the ester group then being removed as described.

The carboxylate salts of the compound of formula I are formed by reacting the carboxyl group of the cephalosporanic acid moiety, i.e., R is hydrogen, with any of the salt forming ions described above.

It will be appreciated that the compounds of formula I are optically active due to the presence of an asymmetric carbon atom indicated by the asterisk. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e., R is hydrogen, sodium or potassium) wherein X is acetoxy or heterothio especially 1-methyl-1H-tetrazol-5-ylthio; R₁ is cyclohexadienyl, phenyl or heterocyclic selected from 2-thienyl, 3-thienyl, 2-furyl, 3-furyl, 2-pyridyl, 3-pyridyl and 4-pyridyl; R₂ is hydrogen or methoxy especially hydrogen; and R₃ is hydrogen or lower alkyl, especially hydrogen or methyl.

The most preferred final compounds are the acids and alkali metal salts of formula I wherein R₁ is 2-thienyl, 3-thienyl or phenyl most especially 2-thienyl; R₂ and R₃ each is hydrogen; and X is heterothio particularly wherein X is

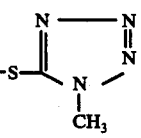

The acid compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter hafniae, Enterobacter cloacae, Klebsiella pneumoniae, Serratia marcescens*, etc. They may be used as antibacterial agents to combat infections due to organisms such as those named above, and in general may be utilized in a manner similar to cephradine and other cephalosporins. For example, a compound of formula I or a physiologically acceptable salt thereof may be used in various animal species in an amount of about 1 to 100 mg/kg., daily, orally or parenterally, in single or two to four divided doses to treat infections of bacterial origin, e.g., 5.0 mg/kg in mice.

Up to about 600 mg. of an acid compound of formula I or a physiologically acceptable salt thereof may be incorporated in an oral dosage form such as tablet, capsule or elixir or in an injectable form in a sterile aqueous vehicle prepared according to conventional pharmaceutical practice.

Illustrative process details are provided in the examples. All temperatures are in degrees celsius.

EXAMPLE 1

[D-α-[(2-Ethoxy-1,2-dioxoethyl)amino]-2-thiopheneacetic acid, diphenylmethyl ester 3.2 g. (20 mM) of 2-D-thienylglycine diphenylmethyl ester are dissolved in 50 ml. of methylene chloride. 1 g. of triethylamine is added and 1.3 g. (20 mM) of oxalic acid chloride ethyl ester in 20 ml. of methylene chloride are added dropwise at −20°. After 2 hours, the reaction solution is shaken with water, dried over sodium sulfate and the solvent is distilled off in vacuum. The residual syrup is the pure product, [D-α-[(2-ethoxy-1,2-dioxoethyl)amino]-2-thiopheneacetic acid, diphenylmethyl ester.

EXAMPLE 2

D-α-[(2-Ethoxy-1,2-dioxoethyl)amino]-2-thiophene acetic acid

To 9.5 g. of D-α-[(2-ethoxy-1,2-dioxoethyl)amino]-2-thiophene acetic acid, diphenylmethyl ester are added 50 ml. of a mixture of trifluoroacetic acid and anisole (4:1) at −10°. The trifluoroacetic acid and anisole are distilled off to yield an oily residue which is taken up in 100 ml. of saturated sodium bicarbonate solution. This is extracted twice with 20 ml. of ether and the aqueous phase is acidified with hydrochloric acid. Repeated extraction with ethyl acetate and evaporation of the ethyl acetate solution yields D-α-[(2-ethoxy-1,2-dioxoethyl)amino]-2-thiophene acetic acid as a brownish syrup which does not crystallize, yield 6.5 g.

EXAMPLE 3

D-α-[(2-Amino-1,2-dioxoethyl)amino]-2-thiopheneacetic acid 6.5 g. of D-α-[(2-ethoxy-1,2-dioxoethyl)amino]-2-thiopheneacetic acid are dissolved in 100 ml. of 5N alcoholic ammonia solution and kept in a glass autoclave at 40°–50° for 10 hours. The reaction mixture is evaporated, the residue is dissolved in water and acidified to yield D-α-[(2-amino-1,2-dioxoethyl)amino]-2-thiopheneacetic acid in the form of white crystals which are recrystallized from water, yield 4.8 g.; m.p. 173°–175°.

EXAMPLE 4

7-β-[[D-[(2-Amino-1,2-dioxoethyl)amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1.2 g. (5mM) of D-α-[(2-amino-1,2-dioxoethyl)amino]-2-thiopheneacetic acid are dissolved in 50 ml. of absolute tetrahydrofuran and 0.5 ml. of triethylamine is added. 0.55 g. (6 mM) of chloroformic acid ethyl ester in 10 ml. of tetrahydrofuran is added dropwise at −10°. After 30 minutes, this reaction solution is added dropwise to a solution of 2.5 g. (5 mM) of 7-amino-3-[[(1-methyl-1H-tetrazol-5-yl)thio]methyl]cephalosporanic acid, diphenylmethyl ester, in 30 ml. of tetrahydrofuran. The mixture is stirred for 3 hours at 5°. The reaction solution is filtered and the filtrate is evaporated to obtain a brown, solid foam which is dissolved in 25 ml. of methylene chloride and treated with charcoal. 200 ml. of ether are poured in whereupon 7-β-[[D-[(2-amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester precipitates as a beige powder, yield 3.2 g., m.p. 106° (dec.).

EXAMPLE 5

7β-[[D-[(2-Amino-1,2-dioxoethyl)amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid 2.3 g. of the product of Example 4 are stirred for 10 minutes at 0° in a mixture of trifluoroacetic acid and anisole (4:1). After evaporating the trifluoroacetic acid and anisole in vacuum, ether is added to the residual oil which then solidifies. The solid is dissolved in 3N sodium bicarbonate solution, filtered and acidified with 2N hydrochloric acid to pH 3. The product, 7β-[[D-[(2-amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, precipitates as a brown powder which is dried, dissolved in tetrahydrofuran, treated with charcoal and the acid is precipitated with ether as a light beige powder, yield 0.78 g., m.p. 158°–161°.

EXAMPLE 6

D-α-[(2-Amino-1,2-dioxoethyl)amino]-2-thiopheneacetyl chloride 2.3 g. of D-α-[(2-amino-1,2-dioxoethyl)amino]-2-thiopheneacetic acid are suspended in 80 ml. of acetonitrile and 1.2 g. of thionyl chloride are added all at once at −20°. The temperature is allowed to rise to room temperature and the solvent is distilled off in vacuum. The sticky, brownish residue is treated with ether to obtain a light beige, solid powder. The infrared spectrum shows the desired acid chloride which is used immediately since decomposition occurs on storage.

EXAMPLE 7

7β-[[D-[(2-Amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid 2.2 g. (7.5 mM) of D-α-[(2-amino-1,2-dioxoethyl)amino]-2-thiopheneacetyl chloride are added at −10° to a solution of 2.5 g. (7.5 mM) of 7-amino-3-[[(1-methyl-1H-tetrazol-5-yl)thio]methyl]cephalosporanic acid and 3.7 g. of bistrimethylsilyl acetamide in 100 ml. of acetonitrile. The mixture is stirred for one hour and the solvent is then distilled off. The residue is taken up in 50 ml. of methanol and 1 ml. of 2N hydrochloric acid, treated with charcoal. The crude product, 7β-[[D-[(2-amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid is obtained as a beige powder which is reprecipitated from tetrahydrofuran/ether, m.p. 156°–158° and is identical with the product of Example 5.

EXAMPLE 8

7β-[[D-[(2-Amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt The product of Example 5 is reacted with an equimolar aqueous solution of potassium bicarbonate to obtain 7β-[[D-[(2-amino-1,2-dioxoethyl)amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt as a brownish powder, m.p. 174°–175°.

EXAMPLE 9

7β-Amino-3-[[(1-methyl-1H-tetrazol-5-yl)thio]methyl]-8-oxo-5-thia-1-azabicyclo[4.2.0]oct-2-ene-2-carboxylic acid To a stirred suspension of 27.2 g. 7-aminocephalosporanic acid (0.1 mole) in 150 ml. of acetone and 100 ml. of H₂O at 0°–5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warm to room temperature. The stirred mixture is then maintained at 60° (internal temperature) under nitrogen for 3 hours at pH 7–7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

EXAMPLE 10

7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from Example 9, 10.3 g. (0.054 mole) p-toluenesulfonic acid monohydrate, 350 ml. of dioxane (dried by passage through basic alumina), and dry $CH_3OH$ is stirred at room temperature under nitrogen for 30 minutes. The clear solution is evaporated to a residue, and water and $CH_3OH$ are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ in 250 ml. of water. The $CH_2Cl_2$ layer is washed with water and saturated NaCl, and finally dried ($M_gSO_4$) to give a residue after removal of the solvent in vacuo. Treatment of the residue with $Et_2O$ gives a solid (27 g.). Column chromatography of this solid on silica gel by elution with $CHCl_3$ and then $EtOAc-CHCl_3$ (4:1) provides the desired product as a residue (12.9 g.). Treatment with EtOAc then provides 8.0 g. of the desired product as a pale yellow powder.

EXAMPLE 11

DL-α-[(2-Ethoxy-1,2-dioxoethyl)amino]phenylacetic acid, diphenylmethyl ester

By substituting DL-α-aminobenzeneacetic acid, diphenylmethyl ester, for the 2-D-thienylglycine, diphenylmethyl ester in the procedure of Example 1, DL-α-[(ethoxy-1,2-dioxoethyl)amino]phenylacetic acid, diphenylmethyl ester is obtained as a thick colorless oil.

EXAMPLE 12

DL-α-[(2-Amino-1,2-dioxoethyl)amino]phenylacetic acid, diphenylmethyl ester

A mixture of 10mM of DL-α-[(2-ethoxy-1,2-dioxoethyl)-amino]phenylacetic acid, diphenylmethyl ester in 50 ml. of ethanol containing 13mM of ammonia is stirred for 15 minutes. After a short time, a thick slurry forms. The product, DL-α-[(2-amino-1,2-dioxoethyl)amino]phenylacetic acid, diphenylmethyl ester, is filtered off and recrystallized from toluene in the form of white filaments, m.p. 168°.

EXAMPLE 13

DL-α-[(2-Amino-1,2-dioxoethyl)amino]phenylacetic acid 13 g. of the product of Example 12 are added to 250 ml. of a 6N solution of hydrochloric acid in glacial acetic acid. After stirring for 15 minutes everything dissolves. The reaction solution is evaporated at room temperature and the white crystalline residue is triturated with ether, filtered under suction and recrystallized from water to obtain DL-α-[(2-amino-1,2-dioxoethyl)amino]phenylacetic acid as white crystals, m.p. 193°.

EXAMPLE 14

7β-[[DL-[(2-amino-1,2-dioxoethyl)amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1.85 g. (7.5 mM) of DL-α-[(2-amino-1,2-dioxoethyl)amino]-phenylacetic acid is made to react with chloroformic acid ethyl ester and 7-amino-3-[[(1-methyl-1H-tetrazol-5-yl)thio]-methyl]cephalosporanic acid, diphenylmethyl ester according to the procedure of Example 4 to obtain the product, 7β-[[DL-[(2-amino-1,2-dioxoethyl)amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester as a beige powder, m.p. 146°.

EXAMPLE 15

7β-[[DL-[(2-amino-1,2-dioxoethyl)amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid By treating the product of Example 14 with trifluoroacetic acid and anisole according to the procedure of Example 5, 7β-[[DL-[(2-amino-1,2-dioxoethyl)amino]-phenylacetyl]amino]-3-[[(1-methyl-1H-tetrazol-5-yl)thio]methyl]-8-oxo-5-thia-1-azabicyclo[4.2.0]oct-2-ene-2-carboxylic acid is obtained as a beige powder, m.p. 153° (dec.).

The sodium salt is obtained as a light beige powder by freeze drying an equimolar aqueous solution of the above acid and sodium bicarbonate, m.p. 175° (dec.).

EXAMPLE 16

DL-α-[(Ethoxy-1,2-dioxoethyl)amino]-2-furanacetic acid, diphenylmethyl ester

By substituting 2-DL-furylglycine, diphenylmethyl ester for the 2-D-thienylglycine, diphenyl methyl ester in the procedure of Example 1, DL-α-[(ethoxy-1,2-dioxoethyl)amino]-2-furanacetic acid, diphenylmethyl ester is obtained as a colorless oil which does not crystallize.

EXAMPLE 17

DL-α-[(2-Amino-1,2-dioxoethyl)amino]-2-furanacetic acid, diphenylmethyl ester

By substituting DL-α-[(ethoxy-1,2-dioxoethyl)amino]-2-furanacetic acid, diphenylmethyl ester in the procedure of Example 12, DL-α-[(2-amino-1,2-dioxoethyl)amino]-2-furanacetic acid, diphenylmethyl ester is obtained as white crystals, m.p. 168°–170° (toluene).

EXAMPLE 18

DL-α-[(2-Amino-1,2-dioxoethyl)amino]-2-furanacetic acid

By substituting DL-α-[(2-amino-1,2-dioxoethyl)amino]-2-furanacetic acid, diphenylmethyl ester in the procedure of Example 13, DL-α-[(2-amino-1,2-dioxoethyl)amino]-2-furanacetic acid is obtained as white crystals, m.p. 174° (water).

EXAMPLE 19

(6R-trans)-7-[[DL-[(2-Amino-1,2-dioxoethyl)amino]-2-furanylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester By substituting DL-α-[(2-amino-1,2-dioxoethyl)amino]-2-furanacetic acid for the D-α-[(2-amino-1,2-dioxoethyl)amino]-2-thiopheneacetic acid in the procedure of Example 4, (6R-trans)-7-[[DL-[(2-amino-1,2-dioxoethyl)amino]-2-furanylacetyl]amino]-3-[[(methyl-1H-tetrazol-5-yl)thio]-methyl]-8-oxo-5-thia-1-azabicyclo[4.2.0]oct-2-ene-2-carboxylic acid, diphenylmethyl ester is obtained as a beige powder, m.p. 81° (dec.).

EXAMPLE 20

(6R-trans)-7-[[DL-[(2-Amino-1,2-dioxoethyl)amino]-2-furanylacetyl]amino]-3-[[(1-methyl-1H-tetrazol-5-yl)thio]methyl]-8-oxo-5-thia-1-azabicyclo[4.2.0]oct-2-ene-2-carboxylic acid By substituting the diphenylmethyl ester obtained in Example 19 in the procedure of Example 5, (6R-trans)-7-[[DL-[(2-amino-1,2-dioxoethyl)amino]-2-furanylacetyl]amino]-3-[[(1-methyl-1H-tetrazol-5-yl)thio]methyl]-8-oxo-5-thia-1-azabicyclo[4.2.0]oct-2-ene-2-carboxylic acid is obtained as a beige powder, m.p. 154° (dec.).

The sodium salt is obtained as a light powder by the procedure of Example 15, m.p. 171° (dec.).

EXAMPLE 21

L-α-[(2-Amino-1,2-dioxoethyl)amino]thiopheneacetic acid, diphenylmethyl ester a) 3.5 g. (10mM) of α-thienylglycine, diphenylmethyl ester, hydrochloride, are suspended in 50 ml. of a mixture of carbon tetrachloride and methylene chloride (2:1). 1.2 g. (10 mM) of oxalyl chloride are added. The mixture is stirred and a stream of nitrogen is passed through at 35° until a clear solution results. The greenish reaction solution containing L-α-[(2-chloro-1,2-dioxoethyl)amino]-thiophenacetic acid, diphenylmethyl ester is decolorized with activated charcoal and used directly in the next step.

b) The reaction solution from part a is added dropwise to a cooled solution (−20°) of 10mM ammonia and 10mM of dimethylaniline in 500 ml. of methylene chloride. After the addition, the reaction mixture is stirred for 15 more minutes, washed with 100 ml. of water, 100 ml. of 2N hydrochloric acid and again with 100 ml. of water, dried and evaporated. The residue is recrystalized from ethanol and then from toluene to obtain the product, L-α-[(2-amino-1,2-dioxoethyl)amino]thiopheneacetic acid, diphenylmethyl ester as white crystals, m.p. 157°-160°; [α]$_D^{20}$= +59.0° (1% in methylene chloride].

EXAMPLE 22

L-α-[(2-Amino-1,2-dioxoethyl)amino]-2-thiopheneacetic acid

L-α-[(2-Amino-1,2-dioxoethyl)amino]-2-thiopheneacetic acid acid is obtained as white crystals by treating the diphenylmethyl ester obtained in Example 21 with ammonia according to the procedure of Example 12, m.p. 140°-141°; [α]$_D^{20}$= +152° (1% in THF).

EXAMPLE 23

7-β-[[L-[(2-Amino-1,2-dioxoethyl)amino]-2-thienylacetyl]amino]-3-[[(1-methyl-1H-tetrazol-5-yl)thio]methyl]-8-oxo-1-azabicyclo-[4.2.0]oct-2-ene-2-carboxylic acid By substituting L-α-[(2-amino-1,2-dioxoethyl)amino]-2-thiopheneacetic acid in the procedure of Example 4 and recrystallizing from isopropanol, 7β-[[L-[(2-amino-1,2-dioxoethyl)amino]-2-thienylacetyl]amino]-3-[[(1-methyl-1H-tetrazol-5-yl)thio]methyl]-8-oxo-1-azabicyclo[4.2.0]oct-2-ene-2-carboxylic acid, diphenylmethyl ester is obtained as a beige powder, m.p. 94° (dec.). By treating this product as in the procedure of Example 5, 7-β-[[L-[(2-amino-1,2-dioxoethyl)amino]-2-thienylacetyl]amino]-3-[[(1-methyl-1H-tetrazol-5-yl)thio]methyl]-8-oxo-1-azabicyclo[4.2.0]-oct-2-ene-2-carboxylic acid is obtained, m.p. 150° (dec.). The sodium salt is obtained by the procedure of Example 15, m.p. 167°-170° (dec.).

EXAMPLES 24–75

Following the procedure of Example 7 but employing the acylating agent A below having the substituents in the following table (which is prepared as described in Examples 1 to 3 and 6) and the 7β-aminocephalosporanic acid Compound B below, one obtains the product C having the same substituents shown in the table. Where appropriate, the protecting group and ester group are removed as in Examples 5 or 7. The salts are produced as in Example 8.

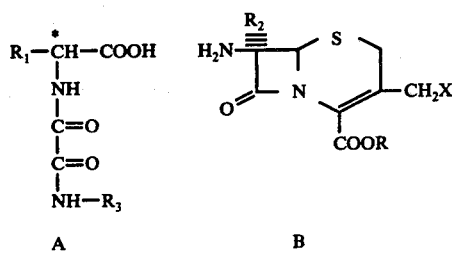

A        B

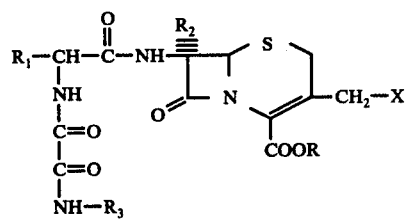

C

| Example | R₁ | R₂ | R | R₃ | X |
|---|---|---|---|---|---|
| 24 | 2-thienyl | H | t-C$_4$H$_9$ | H | -S-(5-methyl-1,3,4-thiadiazol-2-yl) |
| 25 | 2-thienyl | H | H | H | -S-(5-methyl-1,3,4-thiadiazol-2-yl) |
| 26 | 2-thienyl | -OCH$_3$ | -CH$_2$-C$_6$H$_5$ | H | -S-(1-methyl-1H-tetrazol-5-yl) |
| 27 | 2-thienyl | -OCH$_3$ | H | H | -S-(1-methyl-1H-tetrazol-5-yl) |
| 28 | phenyl | H | -CH(C$_6$H$_5$)$_2$ | CH$_3$ | -S-(1-methyl-1H-tetrazol-5-yl) |
| 29 | phenyl | -OCH$_3$ | H | H | -S-(1-methyl-1H-tetrazol-5-yl) |
| 30 | 2-thienyl | H | -CH$_2$CCl$_3$ | C$_2$H$_5$ | -S-(1-ethyl-1H-tetrazol-5-yl) |
| 31 | 2-thienyl | H | CH$_3$ | H | -S-(pyridine-N-oxide-2-yl) |
| 32 | phenyl | H | Na | H | -S-(pyridine-N-oxide-2-yl) |
| 33 | phenyl | -OCH$_3$ | -CH(C$_6$H$_5$)$_2$ | C$_2$H$_5$ | -S-(1-methyl-1H-tetrazol-5-yl) |
| 34 | 2-pyridyl | H | H | H | -S-(1-methyl-1H-tetrazol-5-yl) |
| 35 | 2-thienyl | H | H | H | -O-C(=O)-CH$_3$ |
| 36 | 2-furyl | -OCH$_3$ | -C$_2$H$_5$ | -CH$_3$ | -S-(1-methyl-1H-tetrazol-5-yl) |
| 37 | 2-furyl | H | H | H | -O-C(=O)-CH$_3$ |

-continued

| Example | R₁ | R₂ | R | R₃ | X |
|---|---|---|---|---|---|
| 38 | 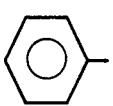 phenyl | H | H | $C_2H_5$ | $-S-CH_3$ |
| 39 | 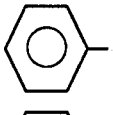 phenyl | $-OCH_3$ | H | H | $-OCONH_2$ |
| 40 | 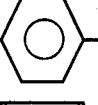 phenyl | H | H | H | 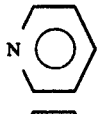 pyridyl |
| 41 | 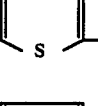 thienyl | $-OCH_3$ | H | H | 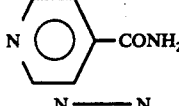 pyridyl-CONH₂ |
| 42 | 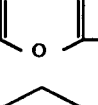 furyl | H | K | H | 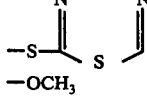 thiadiazolyl |
| 43 | 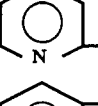 pyridyl | H | $t-C_4H_9$ | $-CH_3$ | $-OCH_3$ |
| 44 | 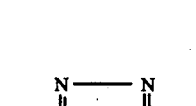 pyridyl | H | $-CH(C_6H_5)_2$ | H | 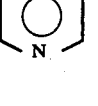 methyltetrazolyl |
| 45 | 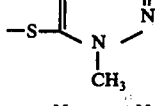 pyridyl | H | K | H | 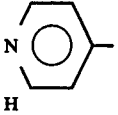 oxadiazolyl-CH₃ |
| 46 | H | H | $-(CH_2)_2C_6H_5$ | H | 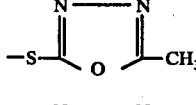 thiadiazolyl |
| 47 | $-C_2H_5$ | $-OCH_3$ | $t-C_4H_9$ | $C_3H_7$ | $-O-\overset{O}{\underset{\|}{C}}-CH_3$ |
| 48 | 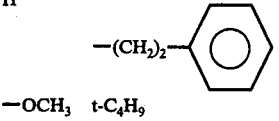 phenyl | H | $-N(C_2H_5)_3$ | H | H |
| 49 | 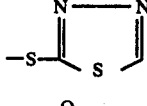 phenyl | H | H | H | $-S-CH_3$ |
| 50 | 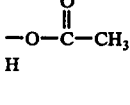 cyclohexyl | H | $-CH(C_6H_5)_2$ | H | 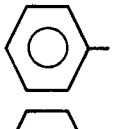 tetrazolyl-NH |
| 51 | 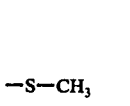 cyclohexyl | $-OCH_3$ | H | H | $-OCH_3$ |
| 52 | 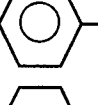 cyclohexenyl | H | $-CH(C_6H_5)_2$ | H | 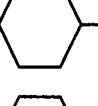 ethyltetrazolyl |
| 53 | 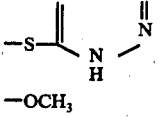 cyclohexenyl | $-OCH_3$ | H | H | 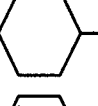 methyltetrazolyl |

-continued
| Example | R₁ | R₂ | R | R₃ | X |
|---|---|---|---|---|---|
| 54 | 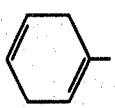 | H | 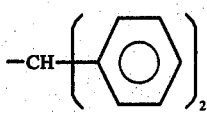 | H | 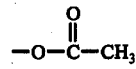 |
| 55 | 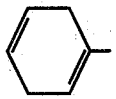 | —OCH₃ | H | H | H |
| 56 | 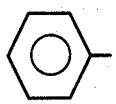 | H | K | 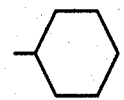 | 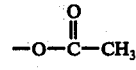 |
| 57 | 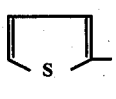 | H | H | 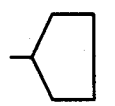 | H |
| 58 | 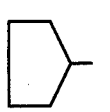 | H | t-C₄H₉ | H | 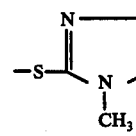 |
| 59 | 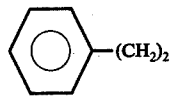 | H | H | H | 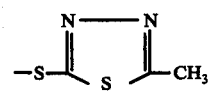 |
| 60 | 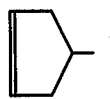 | H | H | CH₃ | 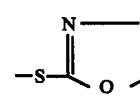 |
| 61 | 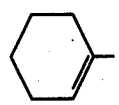 | —OCH₃ | H | H |  |
| 62 | 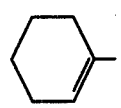 | H | 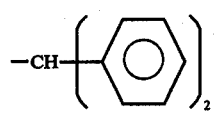 | H | 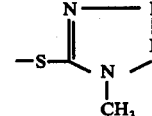 |
| 63 | 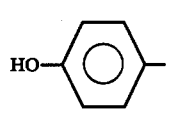 | H | 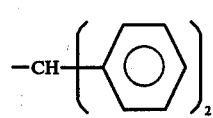 | H | 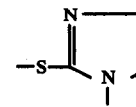 |
| 64 | 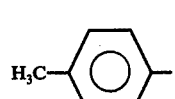 | H | —CH₂—CCl₃ | CH₃ | 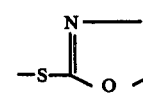 |
| 65 | 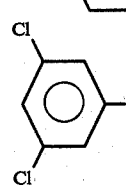 | H | 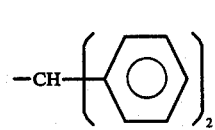 | H | 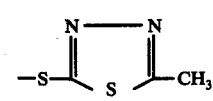 |
| 66 | 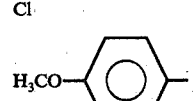 | H | H | H | 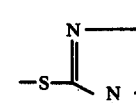 |
| 67 | 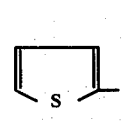 | H | 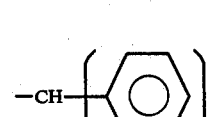 | H | 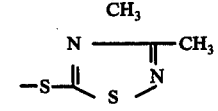 |

| Example | R₁ | R₂ | R | R₃ | X |
|---|---|---|---|---|---|
| 68 | phenyl | —OCH₃ | —CH₂-phenyl | CH₃ | -S-(1-ethyl-triazolyl) |
| 69 | thienyl | H | H | CH₃ | -S-(methyl-thiazolyl) |
| 70 | HO-phenyl | H | H | H | -S-(methyl-oxazolyl) |
| 71 | thienyl | H | H | H | -S-(thiazolyl) |
| 72 | cyclohexenyl | H | Na | H | -S-(thiadiazolyl) |
| 73 | phenyl | H | H | H | -S-(1H-triazolyl) |
| 74 | phenyl | H | H | H | —S—C₂H₅ |
| 75 | phenyl | OCH₃ | Si(CH₃)₃ | H | -S-(1-methyl-tetrazolyl) |

The acylating agents A may be in either the D- or L-form or may be a mixture of D- and L-isomers.

What is claimed is:

1. A compound of the formula

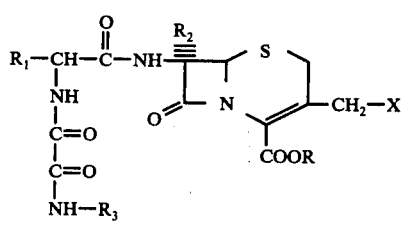

wherein R is hydrogen, lower alkyl, phenyl-lower alkyl, diphenyl-lower alkyl, tri(lower alkyl)silyl, trihaloethyl, aluminum, alkali metal, alkaline earth metal phenyl-lower alkylamine, N-N-dibenzylethylenediamine, lower alkyl amines, triethyl amine, or N-lower alkylpiperidine; R₁ is phenyl, phenyl-lower alkyl, substituted phenyl wherein said phenyl substituent is one or two members selected from the group consisting of halogen, lower alkyl, lower alkoxy, and hydroxy, or a heterocyclic selected from the group consisting of 2-thienyl, 3-thienyl, 2-furyl and 3-furyl; R₂ is hydrogen or methoxy; R₃ is hydrogen, lower alkyl or cycloalkyl of up to 7 carbons; and X is a heterothio group selected from the group consisting of

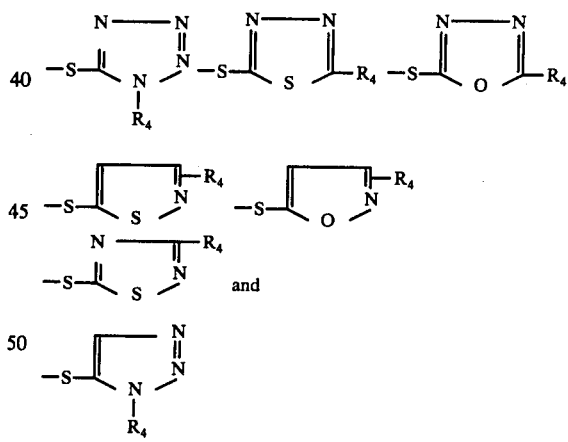

and R₄ is hydrogen or lower alkyl.

2. A compound as in claim 1 wherein R₁ is thienyl.

3. A compound as in claim 1 wherein R₁ is phenyl.

4. A compound as in claim 1 wherein X is methyltetrazolylthio.

5. A compound as in claim 1 wherein R₂ and R₃ each is hydrogen.

6. A compound as in claim 1 wherein R is hydrogen or alkali metal; R₁ is phenyl, thienyl or furyl; R₂ is hydrogen or methoxy; R₃ is hydrogen or lower alkyl; and X is as defined in claim 1.

7. A compound as in claim 1 wherein R is hydrogen, sodium or potassium; R₁ is phenyl or thienyl; R₂ is hydrogen; $R_3$ is hydrogen or methyl; and X is (1-methyl-1H-tetrazol-5-yl)thio.

8. A compound as in claim 1 wherein R, $R_2$ and $R_3$ each is hydrogen; $R_1$ is 2-thienyl; and X is (1-methyl-1H-tetrazol-5-yl)thio.

9. A compound as in claim 1 wherein R is potassium; $R_2$ and $R_3$ each is hydrogen; $R_1$ 2-thienyl; and X is (1-methyl-1H-tetrazol-5-yl)thio.

10. A compound as in claim 1 wherein $R_1$ furyl.

11. A compound as in claim 1 wherein R, $R_2$ and $R_3$ each is hydrogen; $R_1$ is 2-furyl; and X is (1-methyl-1H-tetrazol-5-yl)thio.

12. A compound as in claim 1 wherein R, $R_2$ and $R_3$ each is hydrogen, $R_1$ is phenyl; and X is (1-methyl-1H-tetrazol-5-yl)thio.

* * * * *